(12) United States Patent
Zheng et al.

(10) Patent No.: US 11,793,840 B2
(45) Date of Patent: Oct. 24, 2023

(54) NANO-ARMORED SINGLE CELL PRODUCT FOR TREATING PARKINSON'S DISEASE THROUGH BACTERIA AND A PREPARATION METHOD THEREOF

(71) Applicants: Tangyi Holdings(Shenzhen) Limited, Shenzhen (CN); Healthina Stem Cell Industry Platform (Tianjin) Limited, Tianjin (CN)

(72) Inventors: Bin Zheng, Shenzhen (CN); Yulin Cao, Shenzhen (CN); Wei Sun, Shenzhen (CN); Qinglu Guo, Shenzhen (CN); Shixiang Cheng, Shenzhen (CN)

(73) Assignees: Tangyi Holdings(Shenzhen) Limited, Shenzhen (CN); Healthina Stem Cell Industry Platform (Tianjin) Limited, Tianjin (CN)

( * ) Notice: Subject to any disclaimer, the term of this patent is extended or adjusted under 35 U.S.C. 154(b) by 13 days.

(21) Appl. No.: 17/503,561

(22) Filed: Oct. 18, 2021

(65) Prior Publication Data
US 2023/0065910 A1    Mar. 2, 2023

(30) Foreign Application Priority Data
Aug. 18, 2021   (CN) .......................... 202110950540.6

(51) Int. Cl.
| | | |
|---|---|---|
| *A61K 35/745* | (2015.01) | |
| *A61K 9/127* | (2006.01) | |
| *A61K 35/00* | (2006.01) | |

(52) U.S. Cl.
CPC ............ *A61K 35/745* (2013.01); *A61K 9/127* (2013.01); *A61K 9/1277* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 11,433,102 B2 * | 9/2022 | Borody ................. | A61K 35/38 |
| 2020/0173923 A1 * | 6/2020 | Nolan .................... | G01N 15/06 |

FOREIGN PATENT DOCUMENTS

| | | | |
|---|---|---|---|
| CN | 110122564 | * | 8/2019 |
| CN | 110122564 A | * | 8/2019 |

OTHER PUBLICATIONS

Wyant et al. (University of Michigan, Health Management, 2017). (Year: 2017).*

* cited by examiner

*Primary Examiner* — Celeste A Roney
(74) *Attorney, Agent, or Firm* — Porus IP LLC

(57) ABSTRACT

The present invention discloses a nano-armored single cell product, comprising a liposome and probiotics encapsulated by the liposome, wherein the probiotics are fermented to produce gamma-aminobutyric acid (GABA) that alleviates the activation of an inflammatory response in substantia nigra inducedin a MPTP induced PD model, thus mitigating an inflammatory injury to dopaminergic neurons in substantia nigra and having a neuroprotective effect; encapsulation of the probiotics by the liposome can protect the probiotics from strong acids and digestive enzymes in gastric acid.

1 Claim, 1 Drawing Sheet

US 11,793,840 B2

NANO-ARMORED SINGLE CELL PRODUCT FOR TREATING PARKINSON'S DISEASE THROUGH BACTERIA AND A PREPARATION METHOD THEREOF

FIELD OF THE INVENTION

The present invention relates to the technical field of nano-armored single cells, particularly to a nano-armored single cell product for treating Parkinson's disease through bacteria and a preparation method thereof.

BACKGROUND OF THE INVENTION

Parkinson's disease, the second major neurodegenerative disease in the world, is mainly associated with a variety of neuropathological injuries, such as degeneration of dopaminergic neurons, neuroinflammation and cell apoptosis. Clinically, the main symptoms of Parkinson's disease include static tremor and bradykinesia caused by a neuronal injury. In fact, gastrointestinal symptoms of patients with Parkinson's disease often precede neurological symptoms. The researchers found that the abundance of intestinal floras in patients with Parkinson's disease was significantly different from that in normal people. More and more studies have shown that an intestinal microflora in a microbiota-gut-brain axis plays a vital role in the regulation of a nervous system.

Gamma-aminobutyric acid (GABA) is a short-chain fatty acid (SCFA) derivative and a main inhibitory neurotransmitter in a central nervous system. Studies have shown that GABA can alleviate the activation of an inflammatory response in substantia nigra induced by lipopolysaccharide (LPS) in a PD model (pharmacodynamic model in vivo), thus mitigating an inflammatory injury to dopaminergic neurons in substantia nigra and having a neuroprotective effect. Moreover, reduction of GABA to a lower level in the brain of a patient with Parkinson's disease is also one of the main causes of Parkinson's disease. Therefore, exogenous supply of GABA has become an important means of clinically treating Parkinson's disease.

Compared with injection administration, oral administration of GABA has the advantages of no invasion, no infection, no pain, easy acceptance by patients and the like. However, the oral bioavailability is only 9.81%, and the in-vivo terminal elimination half-life of GABA is 25.1 minutes. In view of the significant role of GABA in the progression of Parkinson's disease, it is necessary to develop an effective GABA delivery method to overcome the problem of low oral utilization and realize the recovery of neurons.

GABA is a fermentation product of probiotics represented by bifidobacteria. The abundance of important short chain fatty acid producing bacteria, i.e. *Bifidobacterium* and *lactobacillus*, is reduced due to a significant change in the intestinal flora of the patient with Parkinson's disease. Therefore, the bacterium producing GABA has a potential value for treating Parkinson's disease.

In recent years, probiotics have been widely used as oral preparations and food additives. They benefit the host by synthesizing and releasing neurotransmitters and regulating the number of SCFA producing bacteria, and they are considered as alternative therapies generally recognized as safe for neurological diseases. However, probiotics can be seriously damaged due to a strong acid and active enzyme environment in gastric fluid, resulting in structural damages and loss of biological activity. Therefore, after reaching the intestinal tract, most bacteria die or are injured seriously, and their metabolic capabilities are seriously damaged, resulting in a limited GABA production capability and unsatisfactory functional recovery of neurons.

At present, coprophilous fungi transplantation and antibiotics mainly improve the output of GABA by improving the abundance of GABA-producing bacterium, but coprophilous fungi transplantation has the problems of complicate operation, strict donor requirements, limited source, instability, low degree of patient acceptance and the like. Antibiotics have many side effects and may also lead to antibiotic resistance and microbiota disorder. Therefore, it is necessary to develop a safer, more convenient and stable method to realize effective delivery of the GABA producing bacterium.

SUMMARY OF THE INVENTION

The present invention aims to provide a nano-armored single cell product for treating Parkinson's disease through bacteria and a preparation method thereof; with full use of the advantages of nano armor and bacterial treatment, the present invention decorates a single living cell with a nano armor coating, which can not only prevent toxic side effects caused by an excessive local GABA concentration, but also maintain GABA within a stable concentration range in the body, thus greatly improving the half-life period and neurological rehabilitation effect.

In order to achieve the above purpose, the present invention provides a nano-armored single cell product, comprising a liposome and probiotics encapsulated by the liposome, wherein the probiotics are fermented to produce gamma-aminobutyric acid (GABA) that alleviates the activation of an inflammatory response in substantia nigra induced by lipopolysaccharide (LPS) in a PD model, thus mitigating an inflammatory injury to dopaminergic neurons in substantia nigra and having a neuroprotective effect; encapsulation of the probiotics by the liposome can protect the probiotics from strong acids and digestive enzymes in gastric acid.

Preferably, the probiotics producing GABA are *Bifidobacterium adolescentis*.

Preferably, the liposome consists of one or more of soy lecithin, cholesterol and vitamin E.

A preparation method of nano-armored single cell product, comprising the following steps:

S1. Preparation of liposome: weighing soy lecithin, cholesterol and vitamin E at a ratio of 4:2:1, putting them in a chloroform solvent, and stirring the solution at room temperature until they are completely dissolved;

Transferring the solution into a round-bottom flask, removing chloroform by reduction vaporization, adding a phosphate buffered solution into the flask, and filtering the solution with a 0.22 μm membrane after ultrasound 10 min to obtain a blank liposome;

Dissolving an appropriate amount of Nile Red in the chloroform, and repeating the above process to generate a Nile Red labeled liposome;

S2. Preparation of LCB: Centrifugalizing 2 mL of a subculture of the *Bifidobacterium adolescentis*, washing at a speed of 3000 rpm, and dissolving precipitate in 1 mL of blank liposome solution; mixing the synthetic liposome and the bacterium in a calcium chloride crosslinking agent for 15 min to synthesize the LCB.

An application of the nano-armored single cell product, wherein the nano-armored single cell product is used in drugs for alleviating and/or treating symptoms of Parkinson's disease in animal bodies.

Preferably, the nano-armored single cell product is used in drugs for alleviating and/or treating symptoms of Parkinson's disease in human bodies.

Preferably, the nano-armored single cell product is used to deliver drugs for alleviating symptoms of Parkinson's disease in human bodies.

Therefore, the present invention uses the nano-armored single cell product for treating Parkinson's disease through bacteria and a preparation method thereof; it selects *Bifidobacterium adolescentis* as a production plant of GABA, and prepares BA(LCB) encapsulated by a liposome through self-assembly of biological interface molecules. The probiotics are encapsulated by the liposome, and the LCB resists the damage of strong acids and digestive enzymes in gastric fluid through a strong hydrophobic effect after wearing a protective "armor". After reaching the intestinal tract, the LCB continuously produces active neurotransmitters (GABA), and the active neurotransmitters enter the brain with blood circulation through intestinal epithelial cells.

This method can not only prevent the toxic side effects caused by excessive local GABA concentration, but also maintain GABA within a stable concentration range in the body, thus greatly improving its half-life and neurological rehabilitation effects. This administration strategy with high efficiency, ultra-long half-life and intelligent adjustable concentration is unimaginable by traditional methods.

The nano-armored single cell is a new drug delivery technology by which a single living cell is decorated with a nano armor coating. By simple self-assembly with the liposome under the condition of cell compatibility, a hydrophobic coating on the surface of each cell serves as an armor to effectively protect the cell from attack and destruction of strong acids and digestive enzymes during treatment of Parkinson's disease with oral administration.

Specifically, the present invention has the advantages that:

(1) The gamma-aminobutyric acid (GABA) produced by the nano-armored single cell product of the present invention is a main inhibitory neurotransmitter in a human body, and the GABA can alleviate the activation of an inflammatory response in substantia nigra induced by lipopolysaccharide (LPS) in a PD model, thus mitigating an inflammatory injury to dopaminergic neurons in substantia nigra and having a neuroprotective effect.

(2) Compared with injection administration, the nano-armored single cell product of the present invention has the advantages of no invasion, no infection, no pain, easy acceptance by patients and the like when GABA is orally administrated.

(3) The nano-armored single cell product of the present invention protects *Bifidobacterium adolescentis* from digestive fluid by the nano armor, continuously produces gamma-aminobutyric acid (GABA), and overcomes the problem of low oral utilization.

The technical solution of the present invention will be further described in detail below through the drawings and embodiments.

DESCRIPTION OF THE INVENTION

Figure 1:
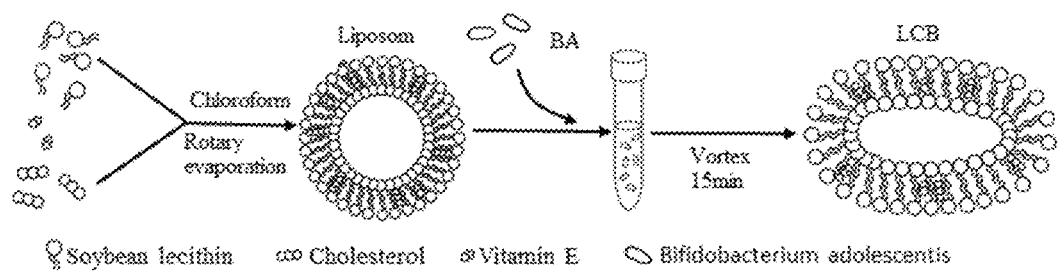
FIG. 1 is a preparation process of the nano-armored single cell product.
Figure 2:
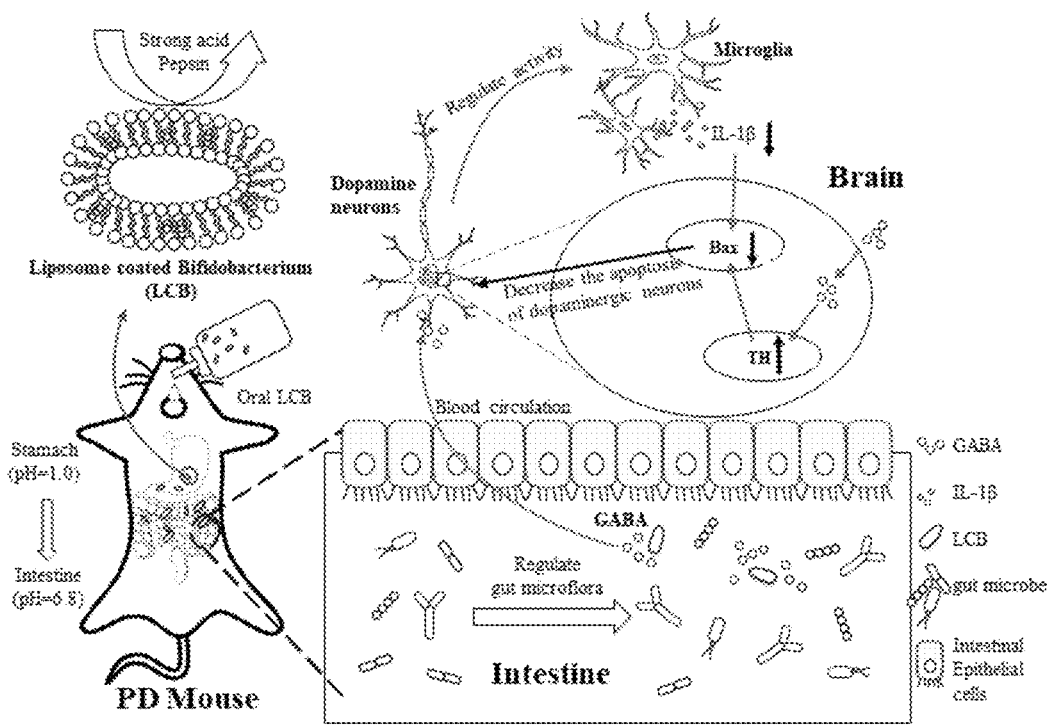
FIG. 2 is a working process of a nano-armored single cell plant.

The technical solution of the present invention will be further described below through the drawings and embodiments.

The description of the exemplary embodiments is merely illustrative and is in no way intended to limit the present disclosure and its application or use. The present disclosure can be implemented in many different forms and is not limited to the embodiments described herein. These embodiments are provided to make the present disclosure thorough and complete and fully express the scope of the present disclosure to those skilled in the art. Note that: unless otherwise stated, the relative arrangement of components and steps, the components of materials, numeric expressions, numerical values and the like set forth in these embodiments shall be interpreted as merely exemplary rather than limitations.

Embodiment I

A nano-armored single cell product, comprising a liposome and probiotics encapsulated by the liposome, wherein the liposome is widely applied to drug delivery; phospholipid and cholesterol as raw materials of the liposome are stable in the oral cavity and the stomach, and can only be decomposed under the catalysis of lipase after reaching the small intestine. Soy lecithin and cholesterol are selected as the liposomes because they can remain in a stable state in the oral cavity and the stomach and can be decomposed in the small intestine so that the probiotics encapsulated in the liposomes can be exposed. It is verified that the liposome can form a stable lipid membrane on the surface of BA, so that living cells can be provided with a strong armor against gastric fluid to ensure the cell activity.

A preparation method of nano-armored single cell product, comprising the following steps:

S1. Preparation of liposome: weighing soy lecithin, cholesterol and vitamin E at the ratio of 4:2:1, putting them in a chloroform solvent, and stirring the solution at room temperature until they are completely dissolved;

Soy lecithin, cholesterol and vitamin E are common materials for preparing the liposome. They can ensure stability in the oral cavity, and can be decomposed in digestive fluid in the gastrointestinal tract to release living cells in the gastrointestinal tract.

Transferring the solution into a round-bottom flask, removing chloroform by reduction vaporization, adding a phosphate buffered solution into the flask, and filtering the solution with a 0.22 μm membrane after ultrasound 10 min to obtain a blank liposome;

Dissolving an appropriate amount of Nile Red in the chloroform, and repeating the above process to generate a Nile Red labeled liposome;

S2. Preparation of LCB: The nano-armored single cell fuses the bacterium and the liposome to encapsulate the liposome on the surface of the bacterium. Centrifugalizing 2 mL of a subculture of the *Bifidobacterium adolescentis*, washing at a speed of 3000 rpm, and dissolving precipitate in 1 mL of blank liposome solution; mixing the synthetic liposome and the bacterium in a calcium chloride crosslinking agent for 15 min to synthesize the LCB.

*Bifidobacterium adolescentis*, capable of producing gamma-aminobutyric acid (GABA) for treating PD and improving the richness of intestinal microorganisms.

Characterization of LCB, wherein the particle size and ζ potential of LCB are measured by dynamic light scattering, the morphology of LCB is observed with a scanning electron microscope, the Nile Red membrane on the surface of LCB is observed with a laser scanning confocal microscope, and the fluorescence intensity of the Nile Red labeled membrane is tested with a flow cytometer.

The nano-armored single cell is used in drugs for alleviating and/or treating Parkinson's disease in animal bodies.

The nano-armored single cell or the preparation method of nano-armored single cell is applied in preparation of medical devices for alleviating and/or treating Parkinson's disease in animal bodies.

The animal bodies are preferably human bodies.

Laboratory Test (1) Test materials

Soy lecithin, cholesterol, vitamin E, HCl, NaOH and CaCl2, purchased from Shanghai Bide Medical Technology Co., Ltd.;

Nile Red, purchased from Tianjin Xiensuopude Technology Co., Ltd.;

Pepsin, trypsin, apoptosis detection kit and DAPI, purchased from Beijing Solarbio Technology Co., Ltd.;

TPY broth, purchased from Qingdao Hope Bio-technology Co., Ltd.;

OPA, acetonitrile, boric acid and 2-mercaptoethanol, purchased from Sigma-Aldrich Shanghai Enzyme-linked Biotechnology Co., Ltd.;

IL-1β assay kit, IL-6 assay kit, TNF-α assay kit, healthy female C57BL/6 and BALB/c mice weighing 15-20 g, purchased from HFK Technology Co. Ltd. (Beijing);

*Lactobacillus plantarum*, donated by Prof. Qi Xianghui from the School of Food and Bioengineering, Jiangsu University.

(2) Preparation of nano-armored single cell

The preparation method of nano-armored single cell product comprises the following steps:

S1. Preparation of liposome: Taking soy lecithin, cholesterol and vitamin E at a certain ratio, putting them in a chloroform solvent, and stirring the solution at room temperature until they are completely dissolved.

S2. Transferring the solution obtained through step S1 into a round-bottom flask, and removing chloroform by reduction vaporization. Adding a phosphate buffered solution into the flask, and filtering the solution with a 0.22 μm membrane after ultrasound 10 min to obtain a blank liposome;

S3. Dissolving an appropriate amount of Nile Red in the chloroform, and repeating the above process to generate a Nile Red labeled liposome;

S4. Preparation of LCB: Centrifugalizing 2 mL of bacterial subculture, washing at a speed of 3000 rpm, and dissolving precipitate in 1 mL of blank liposome solution;

S5. Adding 200 μL of calcium chloride (12.5 mmol/L) and rotating for 15 min for further characterization.

(3) Preparation of control sample: Selecting the *Bifidobacterium adolescentis* not encapsulated by the liposome as the control sample, and other steps are the same as those for preparing the nano-armored single cell.

(4) Taking the control sample and the prepared nano-armored single cell, and comparing the growth of the two bacteria in pepsin simulated gastric fluid (SGF, pH=1.0) and trypsin simulated intestinal fluid (SIF, pH=6.8) and the release of GABA by simulating the environment in intestines and stomach. The environment resistance of LCB is obtained by calculation in different time periods, as shown in Table 1.

TABLE 1

Resistance of BA and LCB to Gastric Fluid Environment

| | The culture solution of pH = 1.0 | | | In SGF (pH = 1.0, pepsin 2 mg/ml) OD (600 nm) | | | SGF 3 h + SIF (pH = 6.8, trypsin 2 mg/ml) OD (600 nm) | | | Highest Proportion of SGF 6 h GABA (H\H0) | Highest Proportion of SIF 6 h GABA (H\H0) |
|---|---|---|---|---|---|---|---|---|---|---|---|
| | 10 min | 30 min | 180 min | 10 min | 30 min | 180 min | 1 h | 3 h | 5 h | | |
| BA | 0.08 | 0.09 | 0.10 | 0.04 | 0.05 | 0.07 | 0.02 | 0.02 | 0.02 | 0.00 | 0.37 |
| LCB | 0.09 | 0.24 | 0.36 | 0.08 | 0.15 | 0.18 | 0.03 | 0.04 | 0.06 | 1.00 | 1.00 |

(5) In the control group, common mice, PD model mice and PD model mice were orally administered with BA. In the case of PD model mice orally administrated with the same concentration of LCB, the content of GABA in vivo is determined. The ratios of other groups are measured with the peak GABA content (H0) of normal mice in the control group as the denominator. It is found that the control sample and the nano-armored single cell preparation plant promote the recovery of dopaminergic neurons in PD mice by releasing the neurotransmitter GABA.

TABLE 2

GABA Contents in Different Groups of Mice

| | Ratio in Blood Ten Days After Oral Administration | Ratio in Brain Ten Days After Oral Administration |
|---|---|---|
| Common mice | 1.00 | 1.00 |
| PD | 0.64 | 0.64 |
| PD + BA | 0.69 | 0.66 |
| PD + LCB | 0.97 | 0.90 |

Therefore, the present invention uses the nano-armored single cell product for treating Parkinson's disease through bacteria and a preparation method thereof; with full use of the advantages of nano armor and bacterial treatment, the present invention decorates a single living cell with a nano armor coating, which can not only prevent toxic side effects caused by an excessive local GABA concentration, but also maintain GABA within a stable concentration range in the body, thus greatly improving the half-life period and neurological rehabilitation effect.

Finally, it should be stated that the above embodiments are only intended to describe the technical solution of the present invention, rather than limiting the technical solution of the present invention. Although the present invention has been described in detail with reference to the preferred embodiments, those of ordinary skill in the art should understand that they can still make amendments to or equivalent substitutions for the technical solution of the present invention, and these amendments or equivalent substitutions cannot keep the amended technical solution departing from the spirit and scope of the technical solution of the present invention.

What is claimed is:

1. A nano-armored single cell product, comprising:
a liposome coated *Bifidobacterium* LCB comprising a liposome and probiotics encapsulated by the liposome,
wherein the probiotics ferment to produce gamma-aminobutyric acid (GABA) that alleviates the activation of an inflammatory response in substantia nigra in a Parkinson's disease (PD) model, thus mitigating an inflammatory injury to dopaminergic neurons in substantia nigra and having a neuroprotective effect; whereby encapsulation of the probiotics by the liposome can protect the probiotics from strong acids and digestive enzymes in gastric acid;
wherein the probiotics producing GABA are *Bifidobacterium adolescentis*;
wherein the liposome comprises soy lecithin, cholesterol and vitamin E;
wherein a preparation method of nano-armored single cell product comprises the following steps:
S1) Preparation of liposome: taking soy lecithin, cholesterol and vitamin E at a ratio of 4:2:1, putting them in a chloroform solvent, and stirring the solution at room temperature until they are completely dissolved;
transferring the solution into a round-bottom flask, removing chloroform by reduction vaporization, adding a phosphate buffered solution into the flask, and filtering the solution with a microporous membrane after ultrasound to obtain a blank liposome;
dissolving an appropriate amount of Nile Red in the chloroform and mixing with the blank liposome to generate a Nile Red labeled liposome;
S2) Preparation of LCB: centrifugalizing 2 mL of a subculture of *Bifidobacterium adolescentis*, washing at a speed of 3,000 rpm, and dissolving precipitate in 1 mL of Nile Red labeled liposome solution; mixing the synthetic liposome and the bacterium in a calcium chloride solution for 15 min to synthesize the LCB; and wherein
the nano-armored single cell product obtained is used in drugs for treating symptoms of PD in animal bodies.

* * * * *